United States Patent [19]

Kukuruzinski

[11] Patent Number: 4,615,349
[45] Date of Patent: Oct. 7, 1986

[54] DISPOSABLE DENTAL FLOSSER

[76] Inventor: Raymond Kukuruzinski, 2800 Quebec St., N.W., Washington, D.C. 20004

[21] Appl. No.: 730,813

[22] Filed: May 6, 1985

Related U.S. Application Data

[63] Continuation of Ser. No. 432,249, Oct. 1, 1982, abandoned.

[51] Int. Cl.⁴ .............................................. A61C 15/00
[52] U.S. Cl. ......................................................... 132/91
[58] Field of Search ................................ 132/91, 92, 93

[56] References Cited

U.S. PATENT DOCUMENTS

| | | | |
|---|---|---|---|
| 1,815,408 | 7/1931 | Jordan | 132/91 |
| 2,187,899 | 1/1940 | Henne | 132/91 |
| 2,516,539 | 7/1950 | Atols | 132/92 R |
| 2,707,782 | 5/1955 | Eby | 132/92 R |
| 3,387,615 | 6/1968 | Mackew | 132/91 |
| 3,926,201 | 12/1975 | Katz | 132/91 |
| 3,974,842 | 8/1976 | Chodorow | 132/91 |

Primary Examiner—Gregory E. McNeill
Attorney, Agent, or Firm—Browdy and Neimark

[57] ABSTRACT

A disposable dental flosser comprises a resilient plastic tuning fork-like holder and a dental floss element secured under tension to the tips of the two prongs of the holder. The ends of the floss element are retained to the holder in an inexpensive yet highly effective way by using corner edge friction resistance factor, i.e. by forcing the ends of the floss element onto and into the surface of the plastic holder by the use of metal staples, rivets or eyelets having a plurality of right angle portions so as to force the ends of the floss element into a torturous, angulated, labyrinthian pattern with a plurality of right angle turns.

10 Claims, 15 Drawing Figures

DISPOSABLE DENTAL FLOSSER

FIELD OF THE INVENTION

The present application is a continuation of prior copending application Ser. No. 432,249, filed Oct. 1, 1982 now abandoned, the entire contents of which are incorporated herein.

The present invention relates to dental flossers and, more particularly, to disposable dental flossers which may be hand held or may be retained in an appliance or handpiece, the latter of which is also part of the present invention and incorporated by reference herein.

BACKGROUND OF THE INVENTION

Dental plaque is believed to be the principal etiological factor in both periodontal disease and dental caries. It initiates an inflammatory process in supporting structures of teeth and if allowed to continue accumulating leads to loss of teeth. Clinical tests of dental plaque maturations show that in many cases after only three days, a thick plaque develops in the interproximal areas of adjacent teeth and gingival margin, and by the sixth day a heavy, gelatinous plaque covers large areas of the tooth surfaces.

The conventional means of removing dental plaque is by mechanical means including brushing and flossing. While chemical and biological agents have been proposed for controlling the bacteria which create the plaque, such agents have so far not achieved great success, and brushing and flossing remain the primary means of controlling plaque. While brushing removes plaque from the major surfaces, it is normally unsatisfactory for effective removal of entrapped food particles and plaque from the inaccessible, interproximal areas of adjacent teeth. Therefore, supplemental daily flossing has been recommended by dentists as an essential factor in the control of dental diseases.

At present, dental floss is generally sold on rollers and spools in dispensers, from which a piece of floss is severed by the user and held between both hands. This takes some development of skill to say nothing of patience and manual dexterity. A length of floss held between the thumb and forefinger of each hand must be stretched taut, inserted between adjacent teeth and moved and up and down to effect the desired cleaning. Another working technique includes wrapping the opposite ends of a floss strand about a finger of each hand and then introducing the two fingers of both hands into the mouth, inserting the floss between adjacent teeth and maneuvering it to effect the desired cleaning. Both procedures are clumsy, unpleasant and time consuming. Consequently, while the great majority of people brush their teeth at least once a day, far too few use dental floss on a daily basis according to a survey by the American Dental Association. The most negligent of those surveyed were adult males, more than forty-five percent of whom did not use floss at all. For this reason gum disease is a problem for up to ninety percent of the adults in this country.

For more than one hundred years there have been attempts to improve and modernize the dental flossing technique by development of holders onto which floss is detachably or permanently secured, and a few hundred patents have already been granted on various flossing devices. These go back to the Shurtleft U.S. Pat. No. 147,987 of 1874, and Wallace U.S. Pat. No. 175,795 of 1876. In general, the dental flossers of the prior art have fallen into two basic categories, namely the reuseable or permanent dental flossers wherein the customer threads the device with floss and then throws away the floss after use, but retains the flosser; and the disposable dental flossers having a structure to which the floss is permanently attached, the entire device being thrown away after one or more uses and replaced by another similar device.

In general, the dental flossers of the permanent type are, as would naturally be expected, of considerably more complex construction and made of more expensive materials. Examples of such devices are those shown in the patents to Munroe U.S. Pat. No. 2,217,917; Storm U.S. Pat. No. 2,059,287; Chamberlin et al U.S. Pat. No. 2,784,722; and Jordan U.S. Pat. No. 1,815,408. Additional examples of such devices are mentioned in parent copending applications Ser. No. 432,249 and/or are cited of record therein.

Disposable flossers, on the other hand, have to be made inexpensively and the floss has to be permanently attached to the flosser in some way. Examples of patents disclosing disposable flossers are the Chodorow U.S. Pat. No. 3,974,842; Katz U.S. Pat. No. 3,926,201; and Henne U.S. Pat. No. 2,187,899. Buscarino U.S. Pat. No. 2,443,415 shows both disposable and permanent flossers. A major problem with disposable flossers of the prior art is the inadequate means of attachment of the floss, because in all cases the prior art requires either complex and expensive, or insufficient means of attachment. Thus, the Chodorow and Katz patents require that the flosser be molded about the floss, which is extremely expensive. Knotting has also been suggested, but this also is expensive and in some cases inadequate. Henne U.S. Pat. No. 2,187,899 suggests various types of mechanical attachment, but none of these provide adequate anchoring; often when floss is forced between two adjacent teeth and the spacing is small, tremendous tensile force is applied and mechanical attachments of this type are not adequate, the floss ends merely pulling from their mechanical anchoring means.

With regard to the molding of the flosser about the ends of the floss, such as shown in the Chodorow and Katz patents, this produces not only a very expensive product, but also limits the types of floss which can be used. For example, medicated and flavored flosses, wherein the medicaments and flavorings are heat sensitive or volatile, cannot be used in the hot molding process because the heat of the operation and the molten plastic will degrade and/or drive off the medicament and/or flavoring material.

As a result, the vast majority of throw away flossers have either failed to undergo successful technological scrutiny of dental appliance manufacturers, market tests, or public acceptance. Thus, the up-to-date dental floss made of nylon fibers and sold in spool-dispensers, which is used according to the primitive flossing procedure described above, is practically the only measure presently available for use by the general public. There are a few permanent flossers which have reached the market place but because of various factors including relatively high cost, these have not achieved great success. Similarly, one disposable flosser is known to be on the market, but this appears to be made by the method of Katz and/or Chodorow, and these flossers are very expensive.

SUMMARY OF THE INVENTION

It is, accordingly, an object of the present invention to overcome deficiencies in the prior art, such as indicated above.

It is another object to provide for the improved ease of flossing in a simple and inexpensive way.

It is a further object to provide a disposable flosser in which the ends of the floss are retained by mechanical means in a strong, effective and inexpensive way.

It is yet another object to provide an effective and convenient disposable dental flosser in which the floss ends are firmly secured under tension by mechanical means, such as flat staples, rivets or eyelets which subject the ends of the floss to an angulated or labyrinthian configuration which resists deanchoring.

It is a further object to provide an inexpensive device for removing dental plaque and food particles from between the teeth and which device is a disposable dental flosser of small size and low cost which can be mass produced with the use of automated machinery at a low cost.

These and other objects in the nature and advantages of the instant invention are achieved by the use of mechanical anchoring means for the ends of the floss, which mechanical anchoring means have right angle corners which deform the floss ends into a plurality of right angled turns thereby defining an angulated or labyrinthian pattern.

BRIEF DESCRIPTION OF DRAWING

Other objects in the nature and advantages of the instant invention will be more apparent from the following detailed description of certain embodiments, taken in conjunction with the drawing, wherein.

DETAILED DESCRIPTION OF EMBODIMENTS

Figure 1:
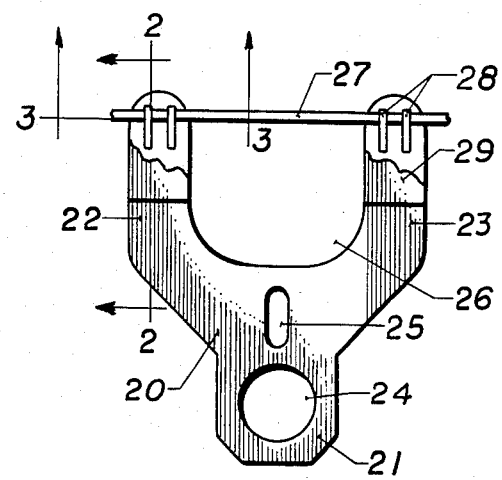
FIG. 1 represents a front view of a disposable dental flosser according to the invention, in large scale, and showing a floss element stretched breadthwise and held with flat staples under tension to the prong tips of the holder.
Figure 2:
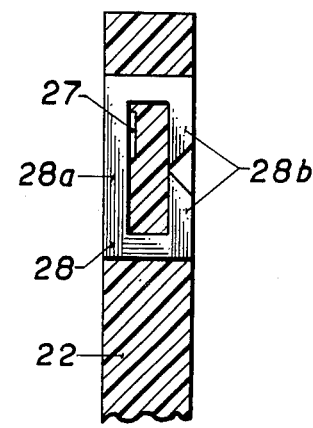
FIG. 2 is a sectional view taken on the line 2—2 of FIG. 1.

Referring now to the drawings, there is shown a disposable dental flosser in which a floss holder 20 of generally Y-configuration and preferably of flat, rectangular cross-section having corners 22a, consists of a handle portion or stem 21 which merges into two tuning-fork like prongs 22 and 23 separated by U space 26. The floss holder 20 is desirably molded or stamped of plastic having a tensile strength of 2.81-3.87 kg/mm$^2$ (4,000-5,500 PSI), and a hardness approximately 40% lower than that of the dental floss material itself. As the most common dental floss material is formed of nylon, most especially nylon 6, and this material has a tensile strength of 7.17-8.44 kg/mm$^2$ (10,200-12,000 PSI) and a Rockwell hardness of about 103-118, it has been found most desirable to form the flosser 20 of high density polyethylene which has a Rockwell hardness of 30-50.

The handle portion 21 comprises a round hole 24 and a longitudinal slot 25 extending therethrough. These are provided for comfortable grip of the handle 21 by the user's thumb and forefinger of one hand for direct manual tooth cleaning, and for attachment of the floss holder 20 to the new and improved handpiece or applicator of the present invention for manual and/or power operation if desired, and for precise location of molded or stamped individual floss holders 20 in automated production lines to accomplish the subsequent manufacturing operations such as securing floss thread or tape to the tips of the holder prongs 22 and 23 as illustrated, followed by sterilization, wrapping, counting and packing as necessary.

The single regular and double extra-fine unwaxed dental floss elements 27, preferably dental tape, are the commercially available elements which are made of nylon fibers and have breaking strengths ranging from about 1.5 kg to over 3.5 kg (3.3 to about 7.7 pounds). According to the invention and as exemplified in the embodiment of FIGS. 1-4, the floss is mechanically anchored such as by staples 28 in a manner explained in more detail below, and with the floss being placed under a tension generally in the range of 0.7-1 kg (1.54 to 2.2 pounds).

A key aspect of the present invention is the manner in which the ends of the floss element 27 are anchored to the tips of the two holder prongs 22 and 23. In all cases, the anchoring means (such as the rectangular or flat staples 28 used in the embodiments of FIGS. 1-8) have generally right angled corners which come into contact to deform the tape as can best be seen in FIG. 3. Considering the embodiment of FIGS. 1-4, the ends of the floss 27 are placed in surface contact with one of the faces of the holder 20 at the indicated location near the tips of the prongs 22 and 23, and the flat hard (metallic) staples 28 are driven into the body of the relatively soft holder 20 thereby causing the so anchored ends of the floss 27 to take the angulated or labyrinthian configuration shown in FIGS. 3 and 4 and described in more detail below. It will be understood that the floss itself, being formed of a harder material than the holder 20, is not weakened by the deformation illustrated in FIG. 3, but is instead caused to assume the tortuous, labyrinthian configuration shown therein having a plurality of right angle turns and wherein the ends of the floss 27 are captured by direct contact between the anchoring means (e.g. the flat staples 28) and the deformed plastic of the holder 20 which resiliently urges its deformed surface against the floss.

Figure 3:
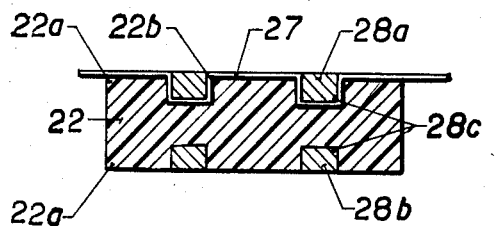
FIG. 3 is a sectional view taken along line 3—3 of FIG. 1.
Figure 4:
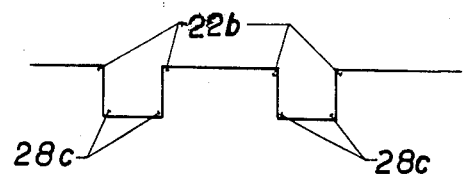
FIG. 4 is a schematic view showing the labyrinthian pattern to which the ends of the floss are subjected to effect anchoring according to the invention as in the embodiment of FIGS. 1-3.
Figure 5:
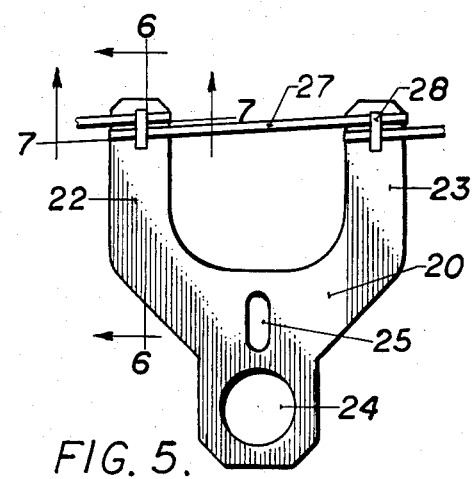
FIG. 5 is a front view similar to FIG. 1 showing a second embodiment of the invention.
Figure 6:
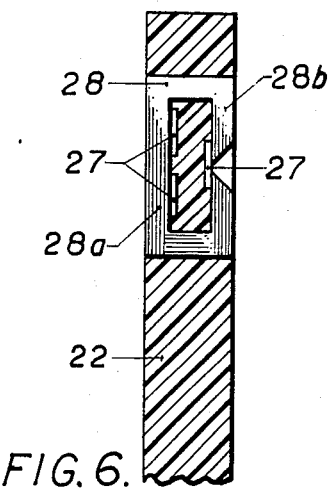
FIG. 6 is a sectional view taken along lines 6—6 of FIG. 5.

The principle by which the excellent anchoring of the instant invention is achieved is known as corner edge friction resistance factor, and for the FIG. 1 embodiment is illustrated in FIG. 3 and schematically illustrated in FIG. 4. As can be seen, each end of the floss 27 is held by two flat staples 28. Each staple, made of flat, rectangular cross-section wire, has a crown 28a and legs 28b. Because of the rectangular cross-section, each staple has a plurality of right angle corners 28c. When the staples are driven home to provide the labyrinthian anchoring as shown in FIGS. 3 and 4, a plurality of right angle turns in the floss 27 are created, including the turns created by the plastic corners 22b of the deformed flosser body and the metal corners 28c of the staples. Noting FIG. 4, it is seen that the two staples create a total of eight right angle turns.

In order to evaluate the angulated floss securing means, the approximate frictional resistance factor values of the corner edges have been determined. For an unwaxed, dry nylon floss interacting with high density polyethylene corner edges 22b with the thickness of the holder 20 being about 1.58 mm (1/16 of an inch) and with flat metal staples 28 having corner edges 28c and having a width of about 0.5 mm (0.02 inches) and a thickness of about 0.35 mm (0.014 inches), the friction resistence factors at different floss thread tensions are as follows:

floss tension 1.0 kg (2.2 pounds): polyethylene corner edge 0.16 kg, steel staple corner edge 0.32 kg;
floss tension 0.75 kg (1.65 pounds): polyethylene corner edge 0.130 kg, steel staple corner edge 0.24 kg;
floss tension 0.5 kg (1.1 pounds): polyethylene corner edge 0.12 kg, steel staple corner edge 0.15 kg;
floss tension 0.35 kg (0.77 pounds): polyethylene corner edge 0.1 kg, steel staple corner edge 0.14 kg.

It will be understood, of course, that the tension values must be added to obtain the total tension at each floss end. For example, in the embodiment of FIG. 1 there are four polyethylene corner edges and four steel staple corner edges. These values of the corner edge friction resistance factors allows one to determine the approximate resistance the anchoring of the ends of the floss will have to a pulling force, i.e. such values provide an approximate floss securing strength value. Again noting FIGS. 3 and 4, and considering the total of 8 right angled turns, an approximate value can be calculated corresponding to the resistance of the anchoring to a pulling force exerted on the floss element, even assuming that the value is only 75 percent of the theorectical value. Thus, taking 0.11 kg for a plastic corner edge 22b and 0.14 kg for a metallic corner edge 28c, the calculated resistance to a pulling force is: 4X 33 0.75×011+4X 0.75×0.14 equals 0.75 kg, and the strength factor of a single angulated floss passageway for FIG. 3 is the ratio of 0.75:0.5, i.e. 1.5 or 150 percent.

Returning to FIG. 1, after anchoring of the ends of the floss 27 to the tips of the prongs 22 and 23 with the flat staples 28, the crowns and bent legs or prongs of the staples 28 may be covered or sealed by an adhesive waterproof tape strip 29 or by a suitable coating composition such as a paint.

The staples 28 may be made with chiseled legs of flat steel wire at the assembly line of the disposable dental flossers. Machinery for making such staples is available.

Tests have been conducted on such flossers to determine the strength of the floss anchoring. Flossers of the type illustrated were suspended with weights attached thereto for from 400 up to 600 hours, the weights corresponding to the above mentioned floss tensions. In come cases, the strength of the staple anchoring means were larger than the breaking strength of the particular floss elements used.

Figure 7:
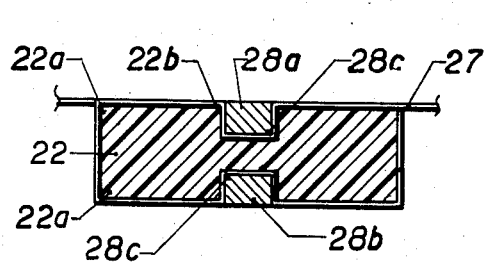
FIG. 7 is a sectional view taken along line 7—7 of FIG. 5.
Figure 8:
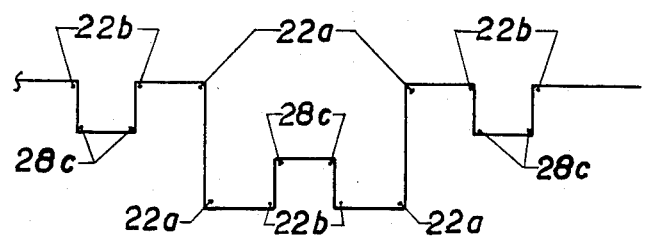
FIG. 8 is a schematic view showing the labyrinthrian pattern to which the anchored ends of the floss are subjected in the embodiment of FIGS. 5-7.
Figure 9:
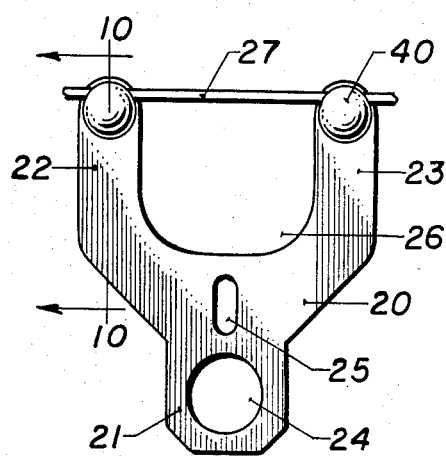
FIG. 9 is a front view of a third embodiment of a disposable dental flosser of the invention wherein the anchoring means is a round-head rivet.
Figure 10:
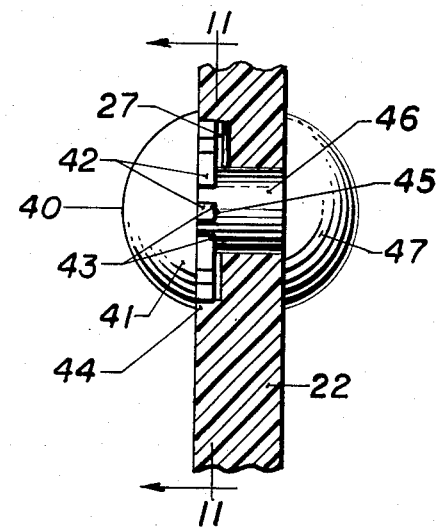
FIG. 10 is a sectional view along line 10—10 of FIG. 9.
Figure 11:
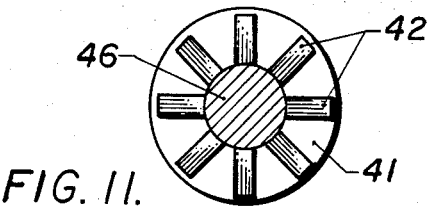
FIG. 11 is a sectional view taken line 11—11 of FIG. 10.
Figure 12:
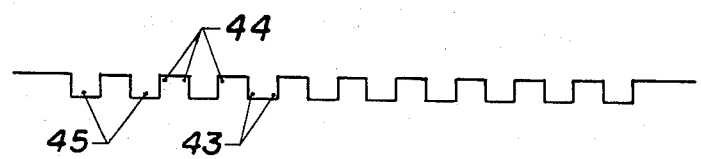
FIG. 12 is a schematic view showing the angulation to which the ends off the floss are subjected by the anchoring means according to the embodiment of FIGS. 9-11.

Considering next the embodiment of FIGS. 5-8, it will be seen that in many ways it is similar to that of FIGS. 1-4, except that in this embodiment only one flat staple 28 is used on each prong 22 and 23, but the floss 27 is wrapped around each prong and passed beneath the staple crown 28a twice. As best seen in FIG. 8, this provides ten plastic corner edges 22a and 22b and six metal corner edges 28c. In that surface visible in FIG. 5, the crown 28a of each staple 28 provides 2 corner edges 28c for each pass of the floss 27, whereas on the opposite side of the flosser (see the cross-section of FIG. 6) there is only pass of the floss which is deformed into the body of the prong 22, 23 by the staple legs 28b which provide two corner edges 28c as shown in FIG. 7. Using the calculation method provided above, it will be seen that even a stronger anchoring is provided in the embodiment of FIGS. 5-8.

The large strength factors achieved according to the present invention provide more than sufficient anchoring of the floss ends regardless of the nature of the floss. For example, various types and strengths of dental floss and dental type can be used, such as regular, fine, extra fine, waxed, unwaxed, medicated, mentholated, etc., and also the floss tensions may be varied considerably, such as 0.25 kg, 0.5 kg, 1 kg, etc., without fear of deanchoring.

Considering next the embodiment of FIGS. 9-12, it is seen that there may be used as anchoring means suitable round head rivets which may be made of low cost materials such as aluminum. The rivets 40 are each provided with a rivet head 41 having an underside provided with projections 42 (see especially FIG. 11), each of the projections 42 having right angle corners 43 (see FIG. 10). The rivets 40 also have a suitable shank 46 and a closing head 47 which may be applied according to conventional practice. In providing the anchoring according to the embodiment of FIGS. 9-12, the dental floss 27 is wrapped around the shank 46 of the rivet clockwise or counter clockwise 450°, and the rivet is then driven into place and the head 47 applied. As with the other embodiments, the force applied serves to drive the floss onto and into the plastic body of the flosser, and the projections 42, each having a pair of right angle corners 43, cause the floss ends to assume the torturous, angulated, labyrithian configuration illustrated in FIG. 12. The depressions in the plastic are given the reference numeral 45 and the edges created by the deformed plastic are given the reference numeral 44.

In the illustrated embodiment of FIGS. 9-12, the rivet head 41 is shown to have eight projections 43, in which case a 450° turn gives 20 right angle metallic corners 43, as well as 20 right angle plastic corners 44. Using the calculation system described above, it is determined that the anchoring given according to FIGS.

9-12 is equal to 1.88 kg (4.14 pounds) exceediing the actual strength of some flosses.

Figure 13:
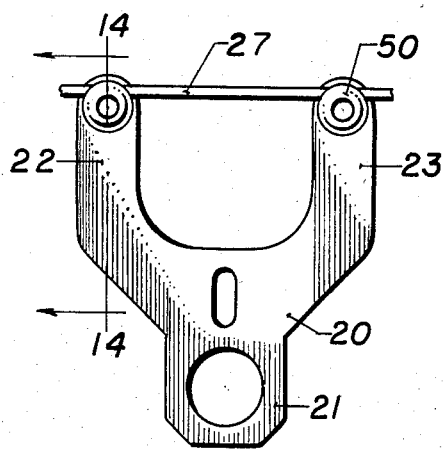
FIG. 13 is a front view of a fourth embodiment of a disposable dental flosser of the present invention wherein the anchoring means is an eyelet.
Figure 14:
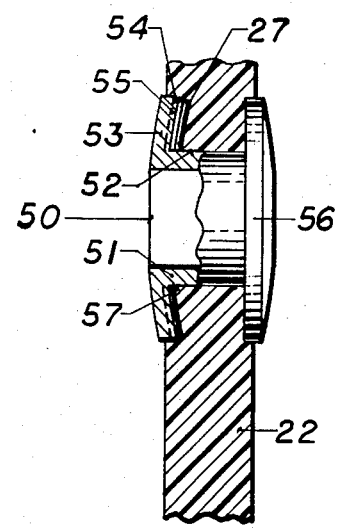
FIG. 14 is a sectional view taken along line 14—14 of FIG. 13.
Figure 15:
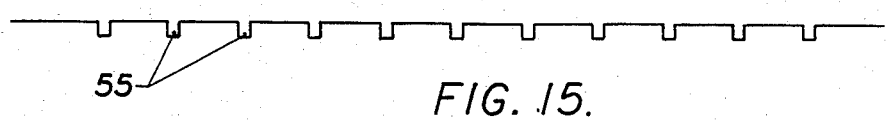
FIG. 15 is a schematic view showing the labyrinthian pattern to which the anchored ends of the floss are subjected according to the embodiment of FIGS. 13 and 14.

FIGS. 13-15 show another embodiment somewhat similar to that of FIGS. 9-12, but using an eyelet 50 as the anchoring means instead of the rivet 40. The eyelet 50 includes an eyelet tube 51 having a neck portion 52 and a flange portion 53 which terminates in a rim 54. Provided on the inner surface of the eyelet flange 53 are a plurality of ridges 55 comparable to the projections 42 in the embodiment of FIGS. 9-12, these ridges each having a rectangular cross-section so as to provide 2 right angle corners. For each eyelet 50 there is provided an eyelet closing element 56.

As with the other embodiments, it will be understood that the ends of the floss 27 are wound about the eyelet neck 52 450° and the eyelets are closed under force such that the body of the plastic of the prongs 22 and 23 is deformed as illustrated in FIG. 14, the ridges 55 of the eyelet driving the floss ends into the angulated pattern schematically shown in FIG. 15. As in the other embodiments of the invention, the angulated, labyrinthian pattern provided creates a very large corner edge friction resistance factor; this provides a firm and permanent anchoring of the floss ends in a secure way.

As with the rivet 40 of FIGS. 9-12, the eyelet of FIGS. 13-15, may be formed of aluminum or other suitable non-corrosive metal.

The important aspects of the invention involve the use of corner edge friction resistance factor, by which a hard anchoring means, having a plurality of right angle corners, drives the floss ends into the relatively softer material of the plastic holder, thereby deforming the plastic holder and creating an angulated, labyrinthian pattern in the floss ends, the floss ends being directly held between the relatively harder right angled anchoring element and the relatively softer holder body, also having a plurality of right angle corners at least some of which are created by the deformation in question, the softer body resiliently urging itself against the hard anchoring material with the floss ends trapped therebetween.

Flossers according to the present invention may vary somewhat in size, but according to one practical embodiment may have dimensions approximately as follows: 32 mm long; 25 mm wide; 1.587-2.043 mm thick; 14 mm U depth; 5 mm prong width; 10 mm handle portion width; 6.35 mm hole 24 inner diameter; 2.38 mm slot 25 width; 4.5 mm slot 25 length. A disposable dental flosser of the above described dimensions can be held and used in a vertical operating position by the user's two fingers. It can be easily moved up and down and along each tooth surface and drawn back and forth accessing 180° around each side of each tooth.

The foregoing description of the specific embodiments will so fully reveal the general nature of the invention that others can, by applying current knowledge, readily modify and/or adapt such specific embodiments without departing from the generic concept, and therefore such adaptations and modifications should and are intended to be comprehended within the meaning and range of equivalents of the disclosed embodiments. The present invention is intended to include other embodiments, including those described in parent application Ser. No. 432,249, the entire contents of which are incorporated by reference herein. It is to be understood that the phraseology or terminology employed herein is for the purpose of description and not of limitation.

What is claimed is:

1. A disposable dental flosser for the removal of plaque from teeth, comprising;
   a body portion including a pair of tuning-fork-like prongs having generally flat planar extremities and which flat extremities each has a generally rectangular cross-section, said flat extremities being in laterally spaced and parallel relationship one another, and being formed of a first relatively soft plastic;
   a dental floss element of a length of at least corresponding substantially to the lateral width of the extremities of the spaced prongs and tightly stretched therebetween in permanent tensioned relationship, each respective end of said floss element being in contact with an outside face of the flat planar surface of said extremities of the prongs, said dental floss element being formed of a second plastic which is relatively hard compared to said first relatively soft plastic;
   and permanent fastening means for permanently and fixedly attaching each end of the dental floss element onto and into the outside face of said flat planar surface of said extremity of each said prong, each said fastening means being formed of a material harder than said relatively soft body portion plastic, and having a flat portion with a rectangular cross-section and which directly engages said floss element forcing said floss element into said flat planar surface of said extremity to resiliently deform said relatively soft plastic and to provide said ends of said floss element with an angulated configuration whereby said floss element ends make a plurality of approximately right angle turns.

2. A disposable dental flosser in accordance with claim 1 wherein said body portion has a Y-shape, and wherein said entire body portion has said flat planar configuration, the leg of said Y extending opposite said prongs serving as a handle portion and having a slot and hole portion therein to facilitate grasping of said handle portion.

3. A disposable floser in accordance with claim 1 wherein said fastening means is formed of metal.

4. A disposable flosser in accordance with claim 3 wherein said fastening means are flat staples.

5. A disposable flosser in accordance with claim 1 wherein said fastening means are rivets.

6. A disposable flosser in accordance with claim 1 wherein said fastening means are eyelet means.

7. A disposable flosser in accordance with claim 1 further comprising adhesive means acting in conjunction with said fastening means.

8. A disposable flosser in accordance with claim 1 wherein said first relatively soft plastic has a Rockwell hardness of about 30-50, and said relatively hard second plastic of said dental floss element has a Rockwell hardness of about 103-118.

9. A disposable flosser in accordance with claim 3 wherein said first relatively soft plastic has a Rockwell hardness of about 30-50, and said relatively hard second plastic of said dental floss element has a Rockwell hardness of about 103-118.

10. A disposable dental flosser according to claim 1 wherein each said floss element end makes at least eight right angle turns.

* * * * *